United States Patent
Erdrich et al.

(10) Patent No.: US 7,368,486 B2
(45) Date of Patent: May 6, 2008

(54) DENTAL MATERIALS WITH HIGH ABRASION RESISTANCE

(75) Inventors: Albert Erdrich, Bad Nauheim (DE); Karl-Heinz Renz, Jettingen (DE); Frank Uwe Stange, Langenargen (DE); Novica Savic, Ranstadt (DE); Cornelia Hermann, Langenargen (DE)

(73) Assignee: Heraeus Kulzer GmbH & Co. KG, Hanau (DE)

( * ) Notice: Subject to any disclaimer, the term of this patent is extended or adjusted under 35 U.S.C. 154(b) by 519 days.

(21) Appl. No.: 10/902,198

(22) Filed: Jul. 29, 2004

(65) Prior Publication Data

US 2005/0059751 A1    Mar. 17, 2005

(30) Foreign Application Priority Data

Jul. 30, 2003    (DE)    ................. 103 35 181

(51) Int. Cl.
*A61K 6/083* (2006.01)
*A61C 5/08* (2006.01)

(52) U.S. Cl. ............ 523/115; 523/116; 433/228.1

(58) Field of Classification Search ........... 523/115; 433/228.1
See application file for complete search history.

(56) References Cited

U.S. PATENT DOCUMENTS

| | | | |
|---|---|---|---|
| 4,389,507 A | 6/1983 | Podszun et al. | 524/460 |
| 4,617,327 A | 10/1986 | Podszun et al. | 523/116 |
| 5,219,899 A * | 6/1993 | Panster et al. | 523/118 |
| 5,548,001 A | 8/1996 | Podszun et al. | 523/116 |
| 6,063,830 A | 5/2000 | Deguchi et al. | 523/115 |
| 6,335,385 B2 * | 1/2002 | Gorlich et al. | 264/17 |
| 2001/0021728 A1 | 9/2001 | Gorlich et al. | 523/115 |

FOREIGN PATENT DOCUMENTS

| | | |
|---|---|---|
| DE | 2850917 A1 | 6/1980 |
| DE | 3000213 A1 | 7/1981 |
| DE | 2462271 C2 | 5/1982 |
| DE | 3135113 A1 | 3/1983 |
| DE | 3316851 A1 | 11/1984 |
| DE | 2849936 C2 | 12/1989 |
| DE | 4004678 A1 | 8/1991 |
| EP | 0677286 B1 | 10/1995 |
| EP | 0962215 A2 | 12/1999 |
| EP | 1 230 906 A1 | 8/2002 |

* cited by examiner

*Primary Examiner*—Tae H Yoon
(74) *Attorney, Agent, or Firm*—Norris McLaughlin & Marcus PA

(57) ABSTRACT

Dental materials with high abrasion resistance and their use for producing artificial teeth and/or their enamel or cutting areas are described. The materials primarily contain:

| | |
|---|---|
| (a) Monofunctional meth-/acrylates | 20-50% |
| (b) Crosslinking meth-/acrylate | 1-20% |
| (c) Splitter polymer from components (2) and (5) | 2-30% |
| (d) PMMA-pearl polymers, partly crosslinked | 2-50% |
| (e) Pyrogenic silicic acid, silanated | 0-20% |
| (f) Inorganically fortified pearl polymer | 5-50% |
| (g) Initiator components | 0.1-1% |
| (h) Coloring pigments | 0.1-3%. |

9 Claims, No Drawings

DENTAL MATERIALS WITH HIGH ABRASION RESISTANCE

The invention concerns abrasion-resistant dental materials and their use for making artificial teeth and/or their enamel or cutting area.

Dental materials with a host of different types of fillers are already established.

The production and composition of a tooth material is described e.g. in U.S. Pat. No. 6,063,830 (Shofu, Kyoto; A). It comprises a combination of silanated silicic acid ($SiO_2$) finely dispersed in urethane dimethacrylate with meth-/acrylate monomers and PMMA copolymers. An amount of 10-70% $SiO_2$ is claimed, relative to the urethane dimethacrylate used. A high abrasion resistance while, at the same time, increased strength is also documented there.

A tooth material that contains an inorganic filler material is known from EP0962215 A2 (GC Dental Corp.; B). In addition to different monomers and crosslinked and non-crosslinked polymers, an inorganic-organic filler complex (1) is contained. Optionally, a second inorganic filler (2) can be contained. For producing the filler complex (1), inorganic filler materials are dissolved and polymerized into meth/acrylate-based monomers. Then, the polymer is broken down by ball milling and used as a ground powder. The fillers (2) can be a variety of glasses known in the dental industry, wherein attention is drawn to the issue of insufficient plaque resistance and silanation is suggested as a remedy.

DE2462271 A1 (Ivoclar, Schaan; C) concerns a material for making dental shaped bodies, including artificial teeth. Silicium dioxide and aluminum oxide are used as filler material in particle sizes of 5-700 nm and an amount of 10-90%. Optionally, the fillers can be silanated.

U.S. Pat. No. 5,548,001 (D1) and U.S. Pat. No. 4,389,507 (D2) (Heraeus Kulzer and/or Bayer AG) concern the production of pearl polymers with inorganic filler components. D1 refers several times to production with crosslinking monomers, whereas D2 describes the possibilities for producing inorganically fortified polymer pearls in general. No possible applications or areas of applications are mentioned.

U.S. Pat. No. 4,617,327 (D3) concerns fillers with an inorganic core, a vinyl silane layer and a second methacrylate polymer layer and the use thereof for making bridges, teeth or fillings with high mechanical strength and great resistance to wear (column 4, pages 19, 20). The fillers are processed together with BisGMA and TEGDMA as well as pigments into artificial teeth, for example.

Tooth material is described in EP0677286 B1 (Heraeus Kulzer; E) that contains barium aluminum silicate glass and microfine silicium dioxide as inorganic fillers. The mixture is made there by adding the silanated fillers to a matrix made from a variety of meth-/acrylates.

In summary, the following commonalities came from prior art:
Various types of meth-/acrylate monomers as well as organic fillers, which can also be partly crosslinked, are used as a matrix.
As a rule, a highly disperse filler is added, in particular silicium dioxide that is optionally in silanated form (A, C, E).
Ground dental glass, preferably silanated (B, E), is used as a filler.
Relevant features of individual documents are:
Use of a splitter polymer as a filler, i.e. inorganic filler is mixed, polymerized and ground in monomer (B)
Use of pearl polymers with an inorganic core and silane layer+methacrylate layer: (D3)

The compositions known from prior art have considerable drawbacks. Some of those are:
Directly adding highly disperse fillers; which automatically have large crosslinkable surfaces, causes:
poor handling properties during the production process due to intense thickening, associated therewith is that less overall filler can be incorporated and/or inhomogenities occur.
a higher affinity to plaque buildup and subsequently discoloration.
Methacrylate-functionalized (silanated) fillers increase the brittleness of the material when added directly to monomer because of their high degree of surface functionality.
Depending on the form, splitter polymers have a very adverse effect on handling properties during production. In addition, specifically when using crosslinked monomers, problems bonding with the plastic matrix can arise later. Another issue is the rougher surfaces caused by the splitter form of the fillers.
Ground dental glass considerably deteriorates the surface quality such that more expensive polishing methods need to be implemented. The hardness of the material increases greatly as well, which is unfavorable in terms of the strains of the prosthesis bearing and resistance to mechanical loads.

Therefore, the goal of the present invention is to at least partially eliminate these drawbacks and, in particular, to achieve the following improvements:
Poor handling properties when using inorganic components, specifically highly fine fillers or even splitter polymers need to be improved. This applies both for storage properties (separation/demixing caused by differences in powder density) as well as for mixture properties, i.e. when processing to a mixture.
A high surface quality should be the goal without expensive polishing.
Bonding issues at the separating layer between the neck/dentin/enamel layers of the artificial tooth need to be alleviated.
Brittleness and a high degree of hardness need to be reduced in favor of a viscoplastic characteristic with abrasion resistance that stays the same.

The task is solved by dental materials of the following composition:

| | |
|---|---|
| (a) Monofunctional meth-/acrylates | 20-50% |
| (b) Crosslinking meth-/acrylate | 1-20% |
| (c) Splitter polymer from components (b) and (e) | 2-30% |
| (d) Pearl polymers, partly crosslinked | 2-50% |
| (e) Pyrogenic silicic acid, silanated | 0-20% |
| (f) Inorganically fortified pearl polymer | 5-50% |
| (g) Initiator components | 0.1-1% |
| (h) Coloring pigments | 0.1-3% |

In the tests performed, contrary to what was expected, it turned out that considerably better product characteristics can be attained with a properly balanced ratio of components in the presence of a specially-designed polymer preliminary stage. This preliminary stage is a methacrylate-based pearl polymer, in which inorganic dental glass is polymerized as filler.

Preferred are dental materials, essentially containing:

| | |
|---|---|
| (a) Monofunctional meth-/acrylates | 25-30% |
| (b) Crosslinking meth-/acrylate | 6-10% |
| (c) Splitter polymer from components (b) and (e) | 12-18% |
| (d) PMMA-pearl polymers partly crosslinked | 15-25% |
| (e) Pyrogenic silicic acid, silanated | 1-5% |
| (f) Inorganically fortified pearl polymer | 20-30% |
| (g) Initiator components | 0.1-1% |
| (h) Coloring pigments | 0.1-3% |

The components of the mixture are explained in more detail as appropriate below: Component (a), (b)-falling under consideration as monofunctional or crosslinked (meth)acrylates are:

Monofunctional or polyfunctional (meth)acrylates, which can be used alone or in mixtures. Examples of such compounds to consider are methylmethacrylate, isobutylmethacrylate, cyclohexylmethacrylate, triethylene glycoldimethacrylate, diethylene glycoldimethacrylate, tetraethylene glycoldimethacrylate, ethylene glycoldimethacrylate, polyethylene glycoldimethacrylate, butandiol dimethacrylate, hexandiol methacrylate, decandiol dimethacrylate, dodecandiol dimethacrylate, bisphenol-A-dimethacrylate, trimethylolpropane trimethacrylate, ethoxylated bisphenol-A-dimethacrylate, but also bis-GMA (2,2-bis-4-(3-methacryloxy-2-hydroxypropyl)-phenylpropane) as well as the reaction products from isocyanates, in particular di- and/or triisocyanates and methacrylates that contain OH-groups, and the appropriate acrylates of all the above compounds. Examples of reaction products of isocyanates are the transformation products of I mol hexamethylene diisocyanate with 2 mol 2-hydroxyethylmethacrylate, of 1 mol (tri(6-isocyanatohexyl)biuret with 3 mol hydroxy ethylmethacrylate and of 1 mol trimethylhexamethylene diisocyanate with 2 mol hydroxyethylmethacrylate, which are also called urethane dimethacrylates. Suitable monomers are the monomers themselves respectively, polymerizable prepolymers made from them as well as mixtures thereof.

Preferred crosslinking monomers are e.g. 2.2-bis-4-(3-methacryloxy-2-hydroxypropyl)-phenyl propane) (bis-GMA), i.e. the transformation product of glycidyl methacrylate and bisphenol-A (containing OH-groups), and 7,7,9-trimethyl-4,13-dioxo-3,14-dioxa-5,12-diazahexadecan-1,16-diyl-dimethacrylate (UDMA), i.e. the urethane dimethacrylate from 2 mol 2-hydroxyethylmethacrylate (HEMA) and 1 mol 2-2,4-trimethylhexamethylene diisocyanate (containing urethane groups). Furthermore, transformation products of glycidyl methacrylate with other bisphenols, like e.g. bisphenol-B (2,2'-bis-(4-hydroxyphenyl)-butane), bisphenol-F (2,2'-methylene diphenol) or 4,4'-dihydroxydiphenyl, as well as transformation products of 2 mol HEMA or 2-hydroxypropyl(meth)acrylate with, in particular, 1 mol, known diisocyanates, such as e.g. hexamethylene diisocyanate, m-xylylene diisocyanate or toluylene diisocyanate are preferred as crosslinking monomers. (Crosslinking meth-/acrylates are by nature compounds with 2 or more methacrylate groups in the monomer.)

(d)—pearl polymers, partially crosslinked, can be PMMA, 2-hydroxyethyl methacrylate-methylmethacrylate copolymer, styrene-maleic acid anhydride copolymer, acrylic polymer, or acrylic acid-maleic acid copolymer. PMMA-pearl polymers are preferred. (f)—The inorganically fortified pearl polymer used as a filler can be one of those described above in D1, D2 and D3. The following composition has preference:

| | |
|---|---|
| Methylmethacrylate | 50-85% |
| Monofunctional methacrylate | 1-10% |
| Silanated glass | 10-40% |

Preferably used as monofunctional monomers should be those that have flexibilizing properties. Those include alkylmeth-/acrylates like ethyl-MA, butyl-MA, ethyl-hexyl-MA, methylacrylate.

Suitable as silanated glass are all the glasses used in the dental sector, e.g. like quartz glass or barium-aluminum silicate glass. The average particle size should be <4 µm since, with larger particles, the abrasion properties (tearing out) and the surface quality suffer. Fillers below 100 nm that are too small do not demonstrate significantly higher abrasion values compared to known materials.

The fillers are produced by means of traditional suspension polymerization. Here, the monomer is predispersed in a water-based phase by adding soap. The inorganic filler is added and integrated into the monomer droplets.

The reaction is induced and the droplets are hardened to pearl polymers by heating the mixture. Benefits of this filler:

The matrix around the filler and the bonding area between matrix and filler is well polymerized and, as a result, very resistant to mechanical loads.

Adding the flexibilizing monomer produces a viscoplastic matrix.

Because the matrix is not crosslinked, in the framework of a swelling process, incorporation into a superior plastic matrix is possible without any problem.

The filler exhibits only slight cloudiness due to the optimized surface tension.

Encapsulating the fillers turns out very smooth surface structures.

On account of the spherical structure, the mixing properties when pasting with monomer is agreeable and a homogenous paste is readily attained.

(g)—The initiators well known to an expert in the field that are suitable for thermal polymerizaton can be considered as initiators. When selecting the initiator, generally the propensity for polymerization of the monomer and the polymerization conditions are taken into consideration. If something like a methacrylate is polymerized at a high temperature, one uses e.g. an organic peroxide like benzoyl peroxide ("BPO"), di-tert-butyl peroxides or cumolhyproxide or an azo compound like 2,2-min-azobisisobutyronitrile or 1,1-min-azo-bis(cyclohexane-1-carbonitrile) is used. For polymerization at room temperature, one purposefully selects redox initiators, like e.g. benzoyl peroxide/dimethylaniline-cumolhydroperoxide/thiourea, ascorbinic acid/Cu salt and organic sulfinic acid (or salt thereof)/amines/peroxides or even tributylborane, e.g. benzoyl peroxide with an aromatic-tertiary amine or tributylborane or tributylborane-partial oxide (TBBO).

(h)—The pigments that are standard in the dental sector and that are well known to an expert in the field are taken into consideration as pigments.

EXAMPLE

The following example arrangement has proven favorable:

| | |
|---|---|
| (a) Monofunctional meth-/acrylates | 26-29.8% |
| (b) Crosslinking meth-/acrylate | 8% |
| (c) Splitter polymer from component (b) and (e) | 15% |
| (d) PMMA-pearl polymers partly crosslinked | 20% |
| (e) Pyrogenic silicic acid, silanated | 2% |
| (f) Inorganically fortified pearl polymers | 25% |
| (g) Initiator components | 0.1-1% |
| (h) Coloring pigments | 0.1-3% |

Production Method

Normal PMMA-based materials are a mix of a colored powder component and a liquid component containing the initiator. Of great importance thereby are proper mix properties, which prevent inhomogenities and porosities from occurring. Then, the paste can be intermediately stored refrigerated, until heat polymerization occurs. When using the composition described above, hardly any changes to the known method are necessary. Traditional coloring and storage of the powder components are possible thanks to the homogeneous miscibility and the not so extreme density differences between PMMA pearls and inorganically filled pearls. Only pyrogenic silicic acid, which is optionally used, is to be dispersed separately into monomer and within the framework of the mixing process.

Use in the Artificial Tooth

In order to achieve an aesthetic of high quality, artificial teeth are made at least 2-layered, but, as a rule, 3-layered (dentin/neck/cutter and/or enamel). The exterior cutting and/or enamel layer is generally exposed to the greatest mechanical strain. High abrasion resistance is inasmuch the most important requirement for this layer. Therefore, the preferred area of use of the material of the invention is within the enamel layer. The layers below that, the dentin layer and the neck layer, usually comprise a purely PMMA-based material, as the most bonding ease to the PMMA prosthesis base is important there.

Consequently the invention also concerns artificial teeth made from the materials of the invention, particularly their cutting area or enamel area.

Metrological Results 1.1 Hardness Measurements

The hardness is determined using a modified Vickers hardness test. In contrast to measuring the dimensions of the indentation after stress is applied, in the Zwick hardness test, the measurement is taken during the application of stress itself. This eliminates accuracy issues when measuring samples with elastic components like plastics.

| Material | Hardness test results (Zwick hardness HZ1) [N/mm$^2$] |
|---|---|
| PMMA tooth material | 150 |
| PMMA tooth material crosslinked with approx. 8-15% crosslinking agent | 160 |
| PMMA tooth material crosslinked, with splitter polymer | 170 |
| PMMA tooth material crosslinked, with highly disperse filler <100 nm | 200 |
| PMMA tooth material crosslinked, with dental glass 0.5-3 µm | 300-400 depending on type |
| Competitor Hard-Resin-Tooth Sirius SHOFU) | 170-180 |
| Comparison composite Dentacolor Sirius (HERAEUS KULZER) | 220 |
| Invention | 140 |

1.2 Flexural Strength, E-module, Impact Strength

The flexural strength and the E-module were determined with EN ISO 1567 prostheses plastics and impact strength as per DIN 53435.

| | PMMA | Comparison composite | Invention |
|---|---|---|---|
| Flexural strength [MPa] | 70 | 80 | 75 |
| E-module [MPa] | 2400 | 3500 | 2700 |
| Impact strength [N/mm$^2$] | 6 | 2.5-3 | 3-4 |

1.3 Abrasion Tests

The most common methods are the 2-body-abrasion test (OCA-2-body-abrasion) and the 3-body-abrasion test (CFA 3-body-abrasion). Both methods comply with the ISO/PDTR14569/2-Dental materials guidance on testing wear.

| | | 3-body abrasion | | |
|---|---|---|---|---|
| | PMMA | Crosslinked PMMA | Comparison composite | Invention |
| Depth CFA 3-body abrasion [µm] | 80 | 60 | 20 | 35 |

| | 2-body abrasion (comparison to hard resin and composites) | | | |
|---|---|---|---|---|
| OCA 2-body-abrasion | PMMA | Competitor Endura (SHOFU) | Comparison composite | Invention |
| Volume loss 120 thsd. cycles [mm$^3$] | 120 | 0.15 | 0.046 | 0.04 |
| Volume loss 240 thsd. cycles [mm$^3$] | | 0.25 | 0.08 | 0.07 |
| Volume loss 480 thsd. cycles [mm$^3$] | | 0.44 | 0.12 | 0.13 |
| Depth [mm] 120 thsd. cycles | 128 | 70 | 72 | |
| Depth [mm] 240 cycles | 174 | 88 | 92 | |
| Depth [mm] 480 thsd. cycles | 231 | 114 | 124 | |

2-body abrasion (comparison to other teeth on the market)

| OCA 2-body abrasion | PMMA SR Orthotype (IVOCLAR) | PMMA crosslinked Premium (HERAEUS KULZER) | PMMA with highly disperse fillers NC Veracia (Shofu) | Invention |
|---|---|---|---|---|
| Volume loss 20 thsd. cycles [mm³] | 3.5 | 0.16 | 1.25 | 0.6 |
| Volume loss 40 thsd. cycles [mm³] | 21.2 | 12.1 | 22.5 | 4 |
| Volume loss 100 thsd. cycles [mm³] | 114.6 | 84.6 | 87 | 21.2 |

A great loss in volume and/or large depth means there is much abrasion. The data clearly shows the higher abrasion resistances of the materials of the invention as compared to the known inorganically filled materials.

At the same, the material hardness is significantly lower and more in the area of the PMMA, which is known to be tough.

Assessment of the Benefits

The benefits gained from using the formula above, particularly also using the fortified pearl polymers are:

Lower material hardness, more elastic structure and high degree of strength.

Thanks to a good bonding of the fillers contained in the polymer pearls high abrasion resistances arise at the level of composites, which is far superior to traditional tooth materials.

Good storage and processing properties, specifically the mixing properties are similar to traditional 2-component systems. Consequently the result is a very homogeneous and defect-free material.

The relatively soft monomer matrix and the pre-encapsulated fillers yield a high material surface quality.

What is claimed is:

1. Dental materials with high abrasion resistance, primarily comprising:

| | |
|---|---|
| (a) Monofunctional meth-/acrylates | 20-50% |
| (b) Crosslinking meth-/acrylate | 1-20% |
| (c) Splitter polymer from components (b) and (e) | 2-30% |
| (d) PMMA-pearl polymers, partly crosslinked | 2-50% |
| (e) Pyrogenic silicic acid, silanated | 0-20% |
| (f) Inorganically fortified pearl polymer | 5-50% |
| (g) Initiator components | 0.1-1% |
| (h) Coloring pigments | 0.1-3%; | wherein PMMA represents polymethyl-methacrylate.

2. Dental materials of claim 1, primarily comprising:

| | |
|---|---|
| (a) Monofunctional meth-/acrylates | 25-30% |
| (b) Crosslinking meth-/acrylate | 6-10% |
| (c) Splitter polymer from components (b) and (e) | 12-18% |
| (d) PMMA-pearl polymers partly crosslinked | 15-25% |
| (e) Pyrogenic silicic acid, silanated | 1-5% |
| (f) Inorganically fortified pearl polymer | 20-30% |
| (g) Initiator components | 0.1-1% |
| (h) Coloring pigments | 0.1-3%. |

3. Dental materials of claim 1, primarily comprising:

| | |
|---|---|
| (a) Monofunctional meth-/acrylates | 26-29.8% |
| (b) Crosslinking meth-/acrylate | 8% |
| (c) Splitter polymer from component (b) and (e) | 15% |
| (d) PMMA-pearl polymers partly crosslinked | 20% |
| (e) Pyrogenic silicic acid, silanated | 2% |
| (f) Inorganically fortified pearl polymers | 25% |
| (g) Initiator components | 0.1-1% |
| (h) Coloring pigments | 0.1-3%. |

4. Artificial tooth comprised of the dental material of claim 1.

5. Artificial tooth comprised of the dental material of claim 2.

6. Artificial tooth comprised of the dental material of claim 3.

7. Artificial tooth comprising a cutting area or an enamel area which consists of a dental material of claim 1.

8. Artificial tooth comprising a cutting area or an enamel area which consists of a dental material of claim 2.

9. Artificial tooth comprising a cutting area or an enamel area which consists of a dental material of claim 3.

* * * * *